(12) United States Patent
McDown et al.

(10) Patent No.: US 10,010,684 B2
(45) Date of Patent: Jul. 3, 2018

(54) SAFETY NEEDLE ASSEMBLY

(75) Inventors: Christopher McDown, San Antonio, TX (US); Eliot Zaiken, Covington, GA (US); Tieming Ruan, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1180 days.

(21) Appl. No.: 12/866,768

(22) PCT Filed: Feb. 4, 2009

(86) PCT No.: PCT/US2009/033059
§ 371 (c)(1),
(2), (4) Date: Nov. 29, 2010

(87) PCT Pub. No.: WO2009/102596
PCT Pub. Date: Aug. 20, 2009

(65) Prior Publication Data
US 2011/0066114 A1    Mar. 17, 2011

Related U.S. Application Data

(60) Provisional application No. 61/028,983, filed on Feb. 15, 2008.

(51) Int. Cl.
*A61M 5/32* (2006.01)
*A61M 5/34* (2006.01)
*A61M 5/50* (2006.01)

(52) U.S. Cl.
CPC ........ *A61M 5/3245* (2013.01); *A61M 5/3243* (2013.01); *A61M 5/326* (2013.01);
(Continued)

(58) Field of Classification Search
CPC .... A61M 5/3243; A61M 5/3245; A61M 5/32; A61M 5/3202; A61M 5/3205; A61M 5/321; A61M 5/50
(Continued)

(56) References Cited

U.S. PATENT DOCUMENTS

| 4,911,693 A | 3/1990 | Paris |
| 4,915,701 A | 4/1990 | Halkyard |

(Continued)

FOREIGN PATENT DOCUMENTS

| DE | 202004017971 U1 | 2/2005 |
| FR | 2616331 A1 | 12/1988 |

(Continued)

*Primary Examiner* — Kami A Bosworth
*Assistant Examiner* — Shefali Patel
(74) *Attorney, Agent, or Firm* — Dickinson Wright PLLC (57) ABSTRACT

A safety needle assembly for an injector is provided herein which, in a first aspect of the subject invention, includes a needle having a distal end formed for injection, a carrier for supporting the needle, and a shield for selectively covering the distal end of the needle. The shield includes at least one through aperture formed therein, wherein the at least one through aperture is superimposed over the distal end of the needle in an initial state prior to the injection. In a further aspect of the subject invention, a safety needle assembly is provided which includes a needle having a distal end formed for injection, a carrier for supporting the needle, and a shield for selectively covering the distal end of the needle. The shield includes a proximal and, a distal end and a sidewall extending therebetween. The sidewall defines a first outer diameter at or adjacent to the distal end of the shield, and the sidewall defines at least one outer diameter greater than the first outer diameter at one or more locations located proximally of the first outer diameter.

9 Claims, 12 Drawing Sheets

(52) U.S. Cl.
CPC ........... *A61M 5/3257* (2013.01); *A61M 5/347* (2013.01); *A61M 5/5086* (2013.01); *A61M 2005/3267* (2013.01)

(58) Field of Classification Search
USPC ................................ 604/111, 192, 197, 198
See application file for complete search history.

(56) References Cited

U.S. PATENT DOCUMENTS

| | | | |
|---|---|---|---|
| 5,106,380 A | | 4/1992 | Lobello |
| 5,167,640 A | | 12/1992 | Balding |
| 5,246,428 A | | 9/1993 | Falknor |
| 5,389,085 A | | 2/1995 | D'Alessio et al. |
| 5,578,014 A | | 11/1996 | Erez et al. |
| 5,688,241 A | * | 11/1997 | Asbaghi ................. 604/110 |
| 6,171,283 B1 | * | 1/2001 | Perez et al. ............. 604/192 |
| 6,203,529 B1 | | 3/2001 | Gabriel et al. |
| 6,485,469 B1 | * | 11/2002 | Stewart ............... A61M 5/3271 604/192 |
| 6,544,234 B1 | | 4/2003 | Gabriel |
| 6,547,764 B2 | | 4/2003 | Larsen |
| 6,986,760 B2 | | 1/2006 | Giambattista |
| 7,147,624 B2 | * | 12/2006 | Hirsiger et al. ............. 604/198 |
| 8,177,745 B2 | | 5/2012 | Brechbuehler et al. |
| 2005/0038392 A1 | | 2/2005 | DeSalvo |
| 2005/0113750 A1 | | 5/2005 | Targell |
| 2005/0148943 A1 | * | 7/2005 | Chevalier ............. A61M 5/326 604/198 |
| 2005/0148944 A1 | | 7/2005 | Hsieh |
| 2006/0100576 A1 | | 5/2006 | Wang |
| 2007/0073224 A1 | | 3/2007 | Dries |

FOREIGN PATENT DOCUMENTS

| | | |
|---|---|---|
| JP | H-08191893 A | 7/1996 |
| JP | 11-319090 A | 11/1999 |
| JP | 2006149513 | 6/2006 |
| JP | 2006-517437 A | 7/2006 |
| WO | WO-2006072807 A1 | 7/2006 |

* cited by examiner

SAFETY NEEDLE ASSEMBLY

This application is a National Stage Application under 35 U.S.C. § 371 of PCT Application No. PCT/US2009/033059, filed Feb. 4, 2009, which claims priority to U.S. Provisional Patent Application No. 61/028,983, filed Feb. 15, 2008.

FIELD OF THE INVENTION

This invention relates to needle assemblies for injectors and, more particularly, to safety needle assemblies.

Safety needle assemblies are known in the prior art including safety pen needle assemblies for use with pen injectors. The assemblies are typically individually mountable to an injector. After injection, the assembly is configured to shield the used needle to prevent a user from inadvertently receiving a "needle stick". Typically, the assembly is formed to be removable from the injector and disposed after use.

Pen needles are of limited length, and prior art safety pen assembly designs have been found obtrusive in limiting visibility of placement of the pen needle against a patient's skin in performing an injection. In addition, a pen needle must be primed prior to use. Medication expelled during the priming procedure has been found to collect within a safety pen needle assembly. During injection, the expelled medication may be undesirably transferred to a patient's skin thereby causing confusion as to whether a dose was properly administered.

SUMMARY OF THE INVENTION

A safety needle assembly for an injector is provided herein which, in a first aspect of the subject invention, includes a needle having a distal end formed for injection, and a carrier for supporting the needle, the carrier being configured for mounting onto an injector. The assembly further includes a shield for selectively covering the distal end of the needle. The shield includes at least one through aperture formed therein, wherein the through aperture is superimposed over the distal end of the needle in an initial state prior to injection. Advantageously, during priming, the through aperture allows medication to pass therethrough, thereby minimizing the amount of expelled medication collected within the safety needle assembly.

In a further aspect of the subject invention, a safety needle assembly for an injector is provided which includes a needle having a distal end formed for injection, a carrier for supporting the needle, the carrier being configured for mounting onto an injector, and a shield for selectively covering the distal end of the needle. The shield includes a proximal end, a distal end and a sidewall extending therebetween. The sidewall defines a first outer diameter at or adjacent to the distal end, and the sidewall defines at least one outer diameter greater than the first outer diameter at one or more locations located proximally of the first outer diameter. Advantageously, with this arrangement, a shield may be provided which is less obtrusive to a user during injection, particularly in observing the point of injection.

As will be appreciated by those skilled in the art, the two aspects discussed above may be used in combination or separately.

These and other features of the invention will be better understood through a study of the following detailed description and accompanying drawings.

DETAILED DESCRIPTION OF THE INVENTION

With reference to the figures, a safety needle assembly 10 is shown which generally includes a carrier or hub 12, a shield 14, and a needle 16. Various configurations of the carrier 12, the shield 14 and the needle 16 may be utilized consistent with the invention described herein. The needle 16 may be rigidly fixed to the carrier 12 or otherwise supported by the carrier 12 directly or through one or more intermediate components. The carrier 12 may also have features 15 provided which allow for mounting onto an injector P, such as threads, a luer-type connector or combinations thereof. Alternatively, the carrier 12 may be integrally formed or rigidly secured to the injector P. The injector P may be a pen injector or a syringe.

The needle 16 may be of any known design, including being a pen needle. Typically, pen needles have a gauge in the range of 29-33 gauge. The needle 16 terminates at a distal end 18, which is configured for injection into a patient. As is known in the art, the needle 16 may have a second, proximal end 17 formed to communicate with contents of the injector P. For example, the second, proximal end 17 may be formed for piercing through a septum of a drug cartridge contained in the injector P in accessing the medical contents therein for injection.

Figure 1:
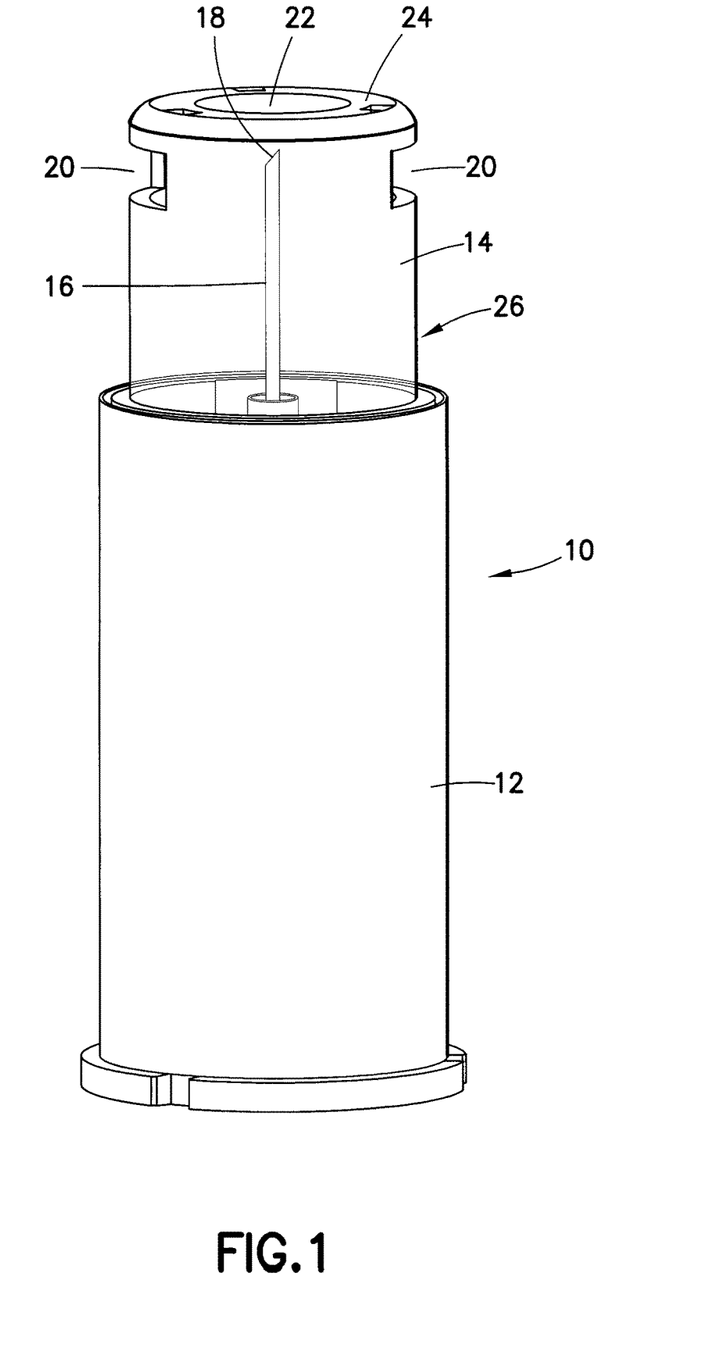
FIGS. 1-7 show different depictions of a through aperture formed in accordance with the subject invention; and, FIGS. 8-11 show different configurations of a shield having a reduced outer diameter in accordance with the subject invention.
Figure 1A:
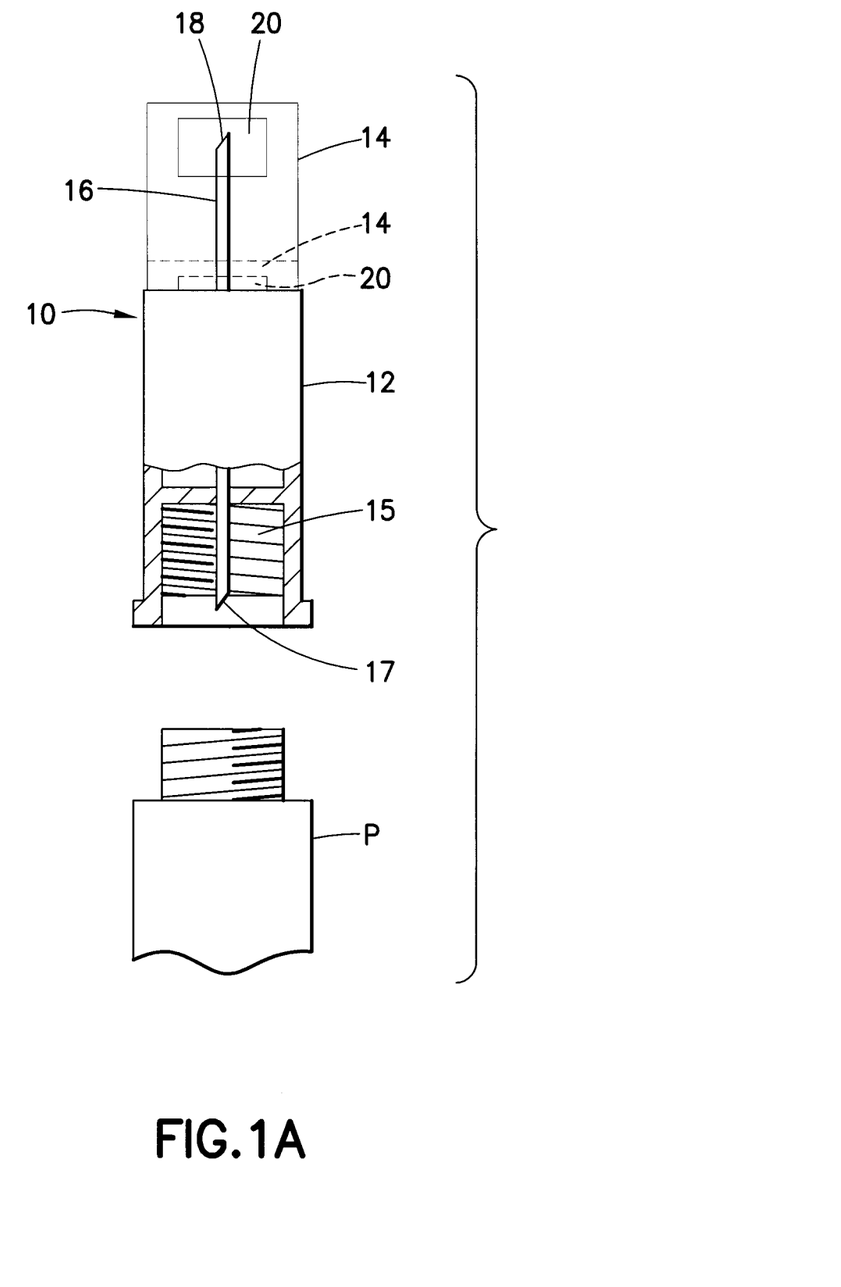
Figure 2:
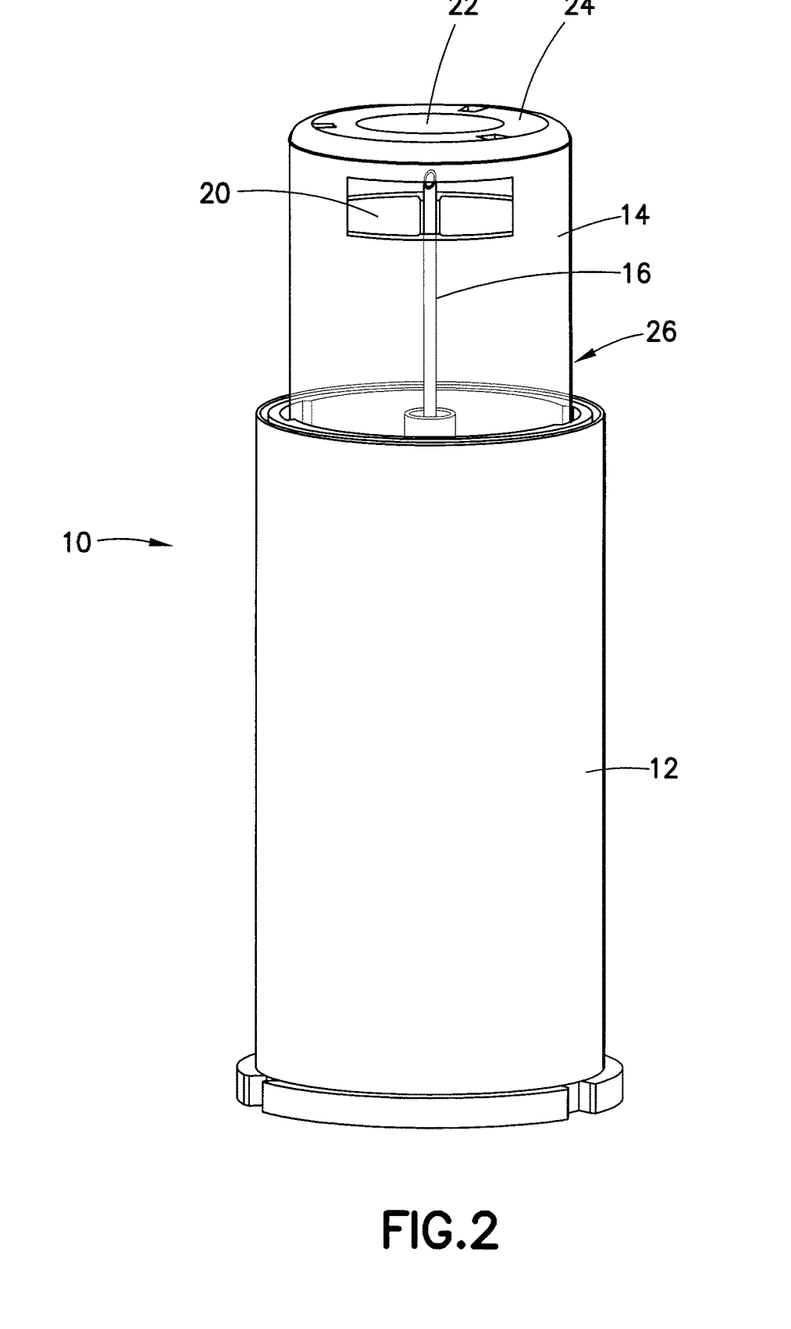
Figure 3:
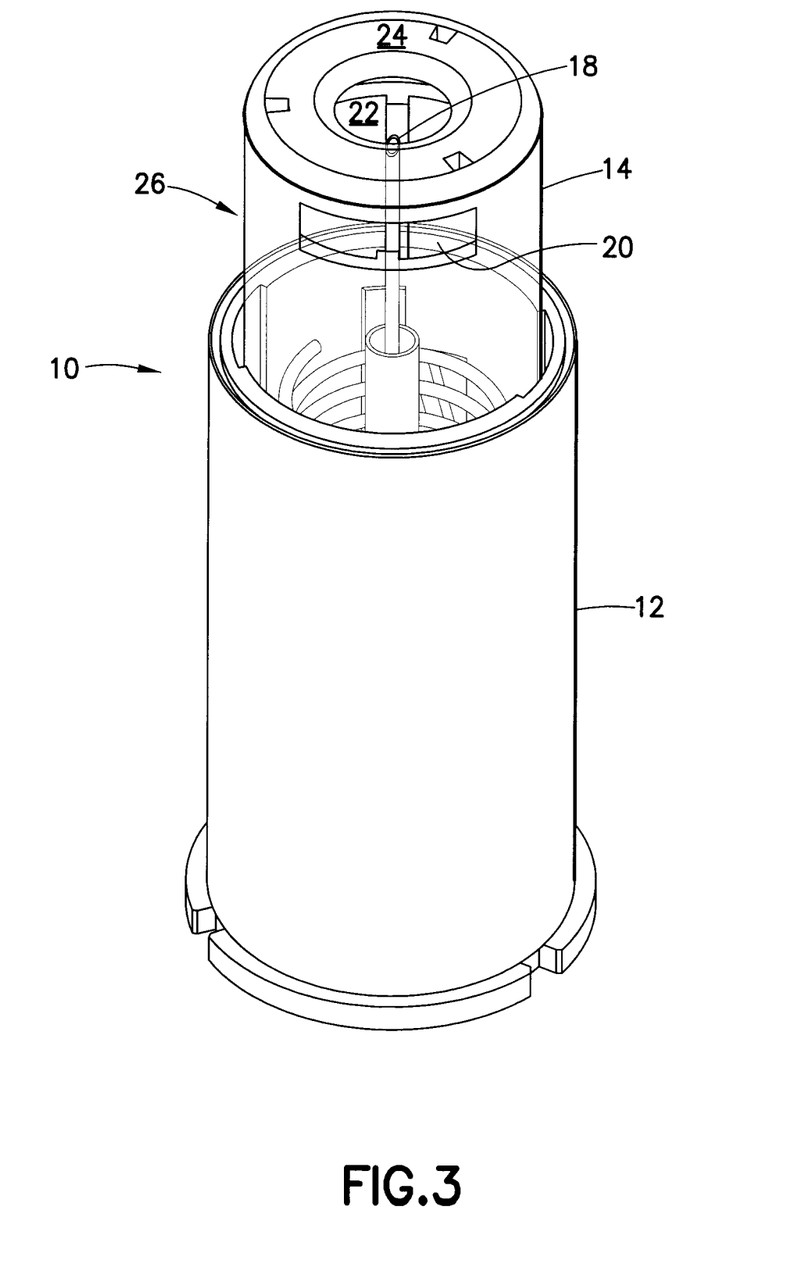
Figure 4:
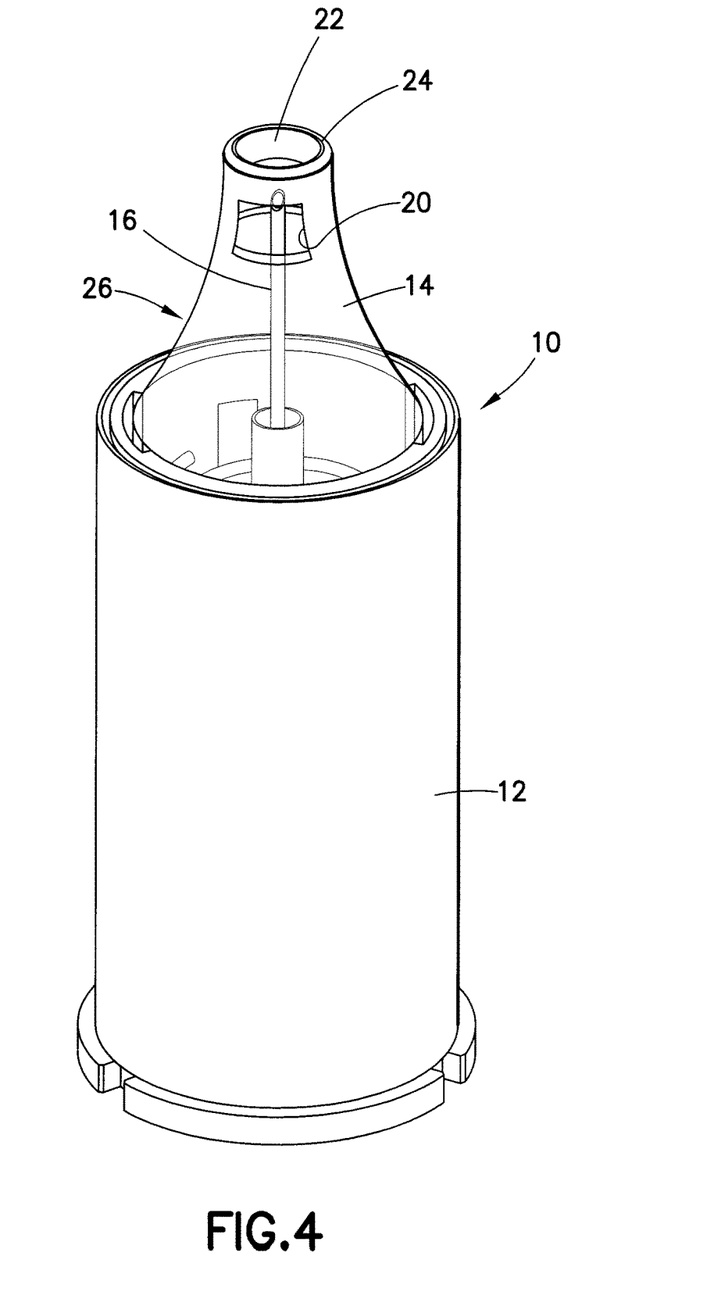
Figure 5:
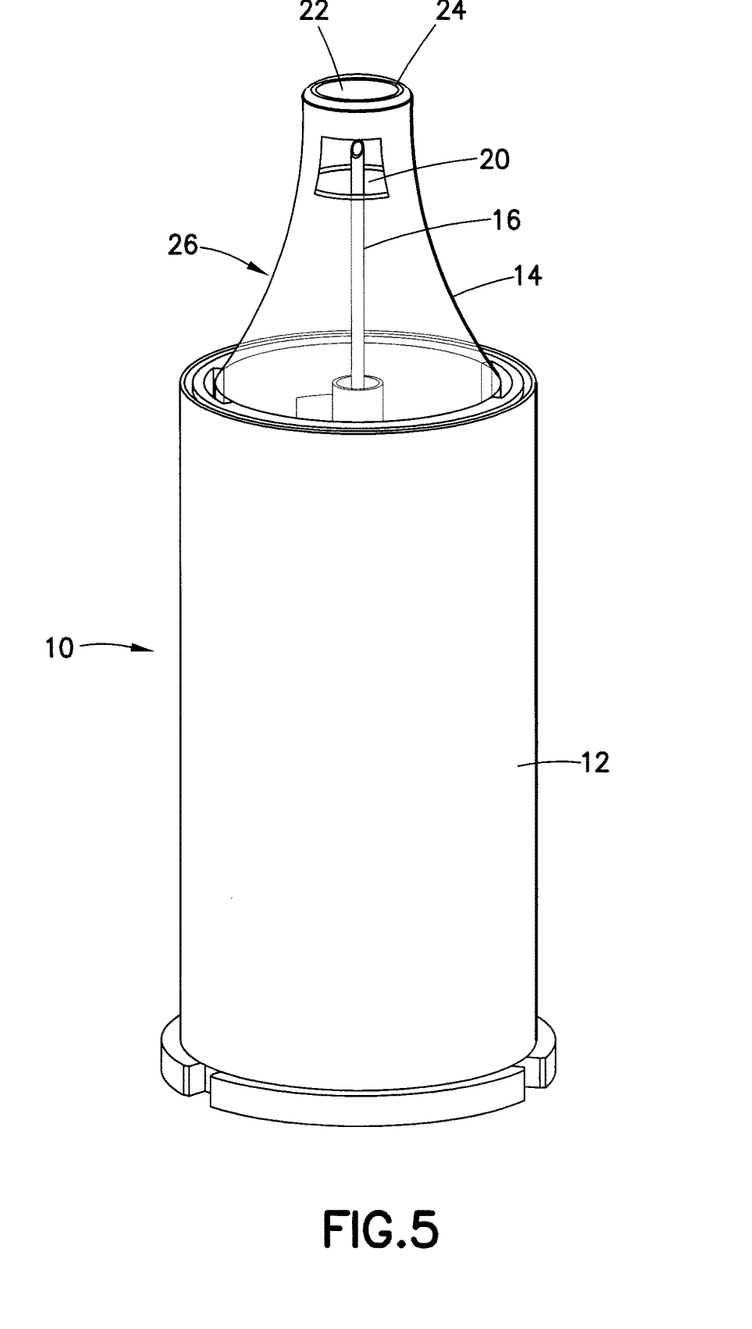

The shield 14 is formed to selectively cover the distal end 18 of the needle 16, particularly after use. It is preferred that the shield 14 cover the distal end 18 prior to use. As such, during use, the shield 14 must be allowed to retract and expose the distal end 18 for injection (as shown by the shield 14 in dashed lines in FIG. 1A). After use, the shield 14 must be driven forwardly to the covered, shielded position and, preferably, locked in the post-use position. Any known arrangement for allowing the shield 14 to be driven rearwardly (proximally) and then forwardly (distally) to a locked position may be used. The shield 14 may move relative to the carrier 12, which is fixed to the injector P. Automated systems ("passive" systems) or systems requiring manual intervention ("active" systems) may be utilized to move the shield 14. As used herein, the term "proximal" shall refer to the direction away from the patient (i.e., non-injection end), while, "distal" shall refer to the direction towards the patient (i.e., injection end).

Safety needle assemblies are known in the art having shields which retract for use from an initial covering position and cover the needle after use (i.e., the shield covers the distal end of the needle before and after use). Examples of such assemblies are found in U.S. Pat. Nos. 5,389,085; 6,203,529; 6,547,764; 6,986,760; and U.S. Published Patent Application. No. 2005/0038392, which are incorporated by reference herein. These shielding arrangements may be utilized with the subject invention.

Figure 6:
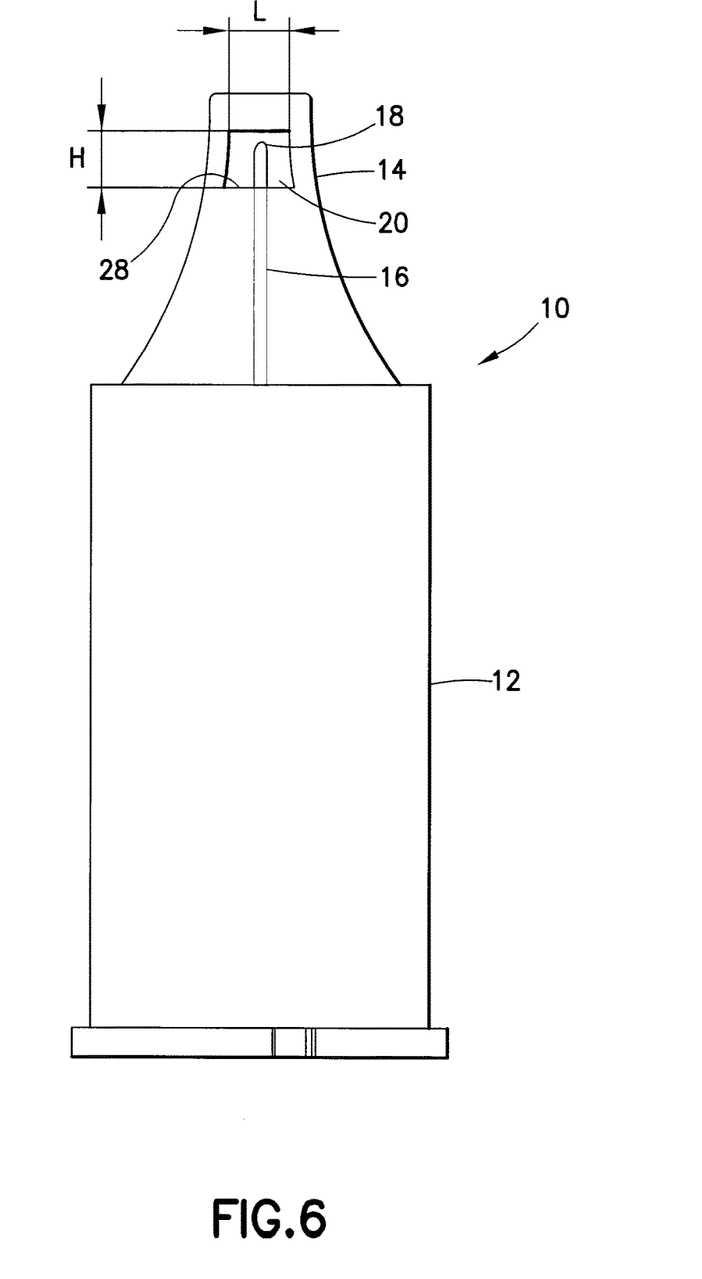

As shown in FIGS. 1-7, in a first aspect of the subject invention, at least one through aperture 20 is formed in the shield 14. As best shown in FIG. 6, in an initial state of the safety needle assembly 10 prior to use, it is preferred that the through aperture 20 be superimposed over the distal end 18 of the needle 16 as viewed along an axis disposed perpendicularly to the needle 16. In this manner, the distal end 18 of the needle 16 is viewable within the footprint of the through aperture 20 as viewed along an axis disposed perpendicularly to the needle 16. With this arrangement, the needle 16 may be primed prior to injection, with medication being expelled from the needle 16 during priming being allowed to escape through the through aperture 20. An opening 22 may be formed in a distal end 24 of the shield 14 to also allow expelled medication to be discharged out of the safety needle assembly 10 during priming. During use, the needle 16 may extend through the opening 22 to allow injection of the distal end 18 into a patient.

For convenience of the user, it is preferred that at least two of the through apertures 20 be provided, which are located diametrically opposite along the circumference of the shield 14. It is preferred that during priming, the needle 16 be oriented horizontally or downwardly so that expelled medication has a greater chance of being discharged through at least one of the through apertures 20.

The shield 14 includes a sidewall 26 which extends proximally from the distal end 24. It is preferred that the through aperture 20 be formed through the sidewall 26 adjacent to or in proximity to the distal end 24. Preferably, the distal end 24 has portions which uninterruptedly span across the through aperture 20. This arrangement provides rigidity at the distal end 24 which offsets at least some loss of rigidity due to the presence of one or more of the through apertures 20. As shown in the figures, the sidewall may be formed with various configurations, e.g., cylindrical, tapered, and so forth.

The through apertures 20 may be formed with different sizes and configurations. With reference to FIG. 6, it is noted that the width L of through aperture 20 should be limited, since an excessively great width will result in excessive weakening of the shield 14. The width L may be in the range of 20%-90% of the circumference of the shield 14 taken at the location of the through aperture 20.

Figure 7:
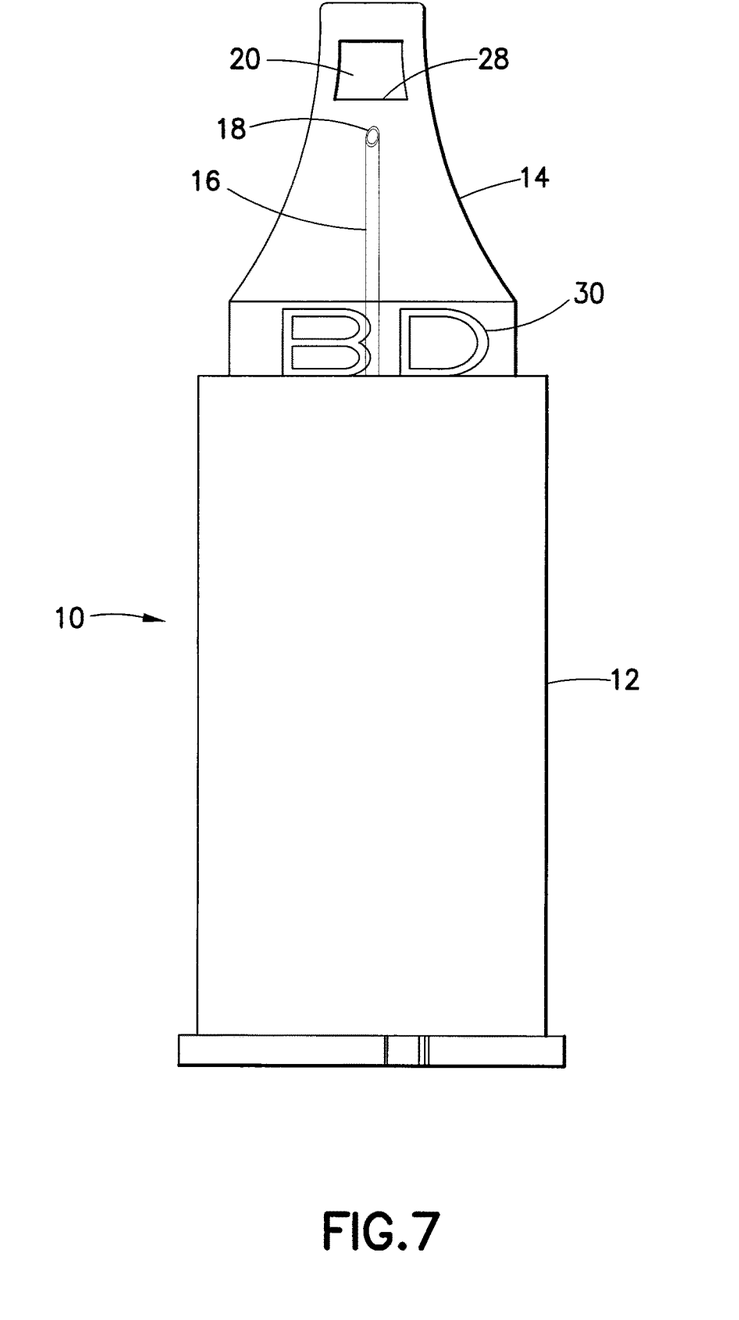

It is preferred that the through aperture 20 have a rectangular configuration with a lower edge 28 being located a distance H from the distal end 18. With reference to FIGS. 6 and 7, the lower edge 28 is preferably located to be proximal of the distal end 18 in an initial state of the safety pen needle assembly 10 prior to use (FIG. 6) and located distally of the distal end 18 after use (e.g., with the shield 14 being in a locked shielded state) (FIG. 7). Thus, the through aperture 20 is located more distally from the carrier 12 after use, then before use. A user may observe the location of the lower edge 28 relative to the distal end 18 and readily determine if there has been use of the safety pen needle assembly 10. The lower edge 28 thus acts as an indicator for indicating usage of the safety needle assembly 10. This is particularly helpful for a safety needle assembly which shields the needle 16 prior to use. As further indication of usage, an insignia (e.g., logo) or other visible feature 30 may be provided on the shield 14 which is covered by the carrier 12 in an initial state (FIG. 6) and exposed in a shielded state (FIG. 7).

As will be appreciated by those skilled in the art, the through aperture 20 permits a user to view the distal end 18 of the needle 16 during priming, even with the shield 14 being formed of opaque material. The through aperture 20 also permits a user to visually confirm the geometry of the needle 16.

With reference to FIGS. 8-11, in a second aspect of the subject invention, the shield 14 may be formed such that the sidewall 26, on an outer surface 32 thereof, has a reduced outer diameter D1 at or adjacent to the distal end 24 as compared to proximally-located portions of the shield 14. The sidewall 26 extends between the distal end 18 and a proximal end 36 of the shield 14 with the outer surface 32 facing away from a longitudinal axis 34 of the shield 14. The distal end 24 and the proximal end 36 are disposed to face generally, distally and proximally, respectively, along the longitudinal axis 34.

Figure 8:
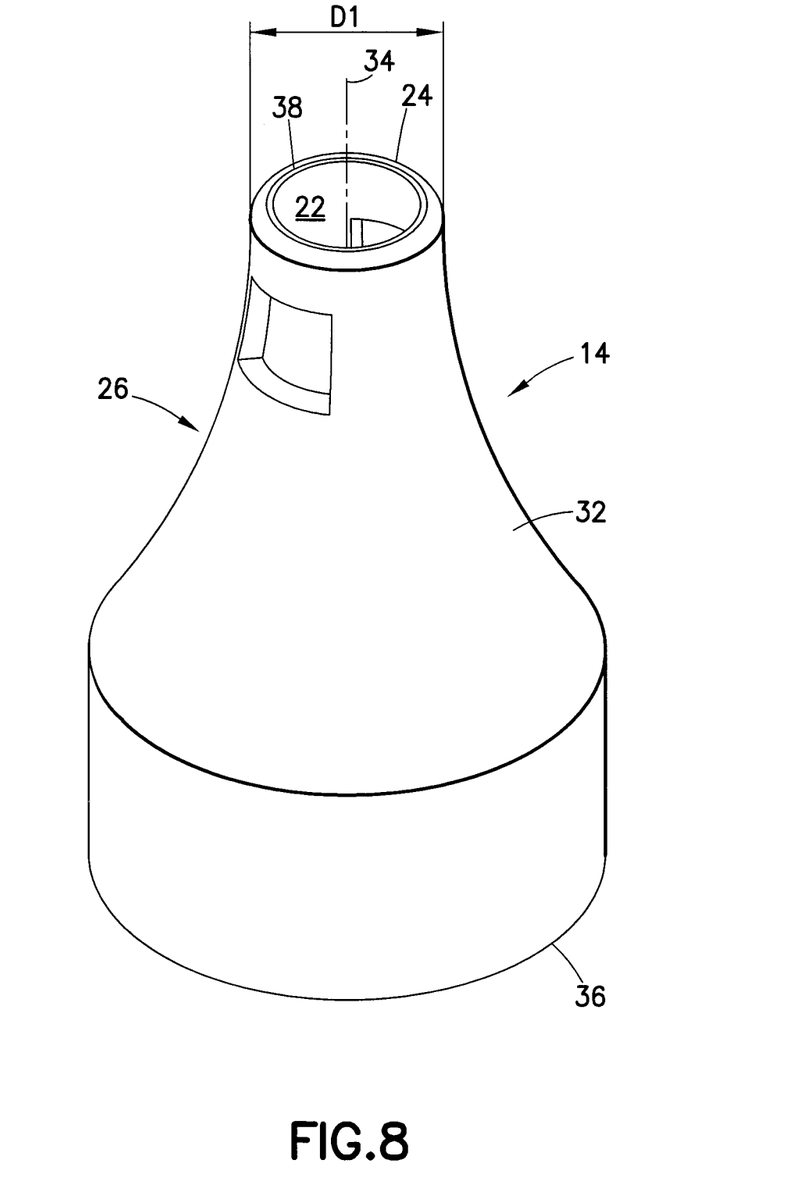
Figure 9:
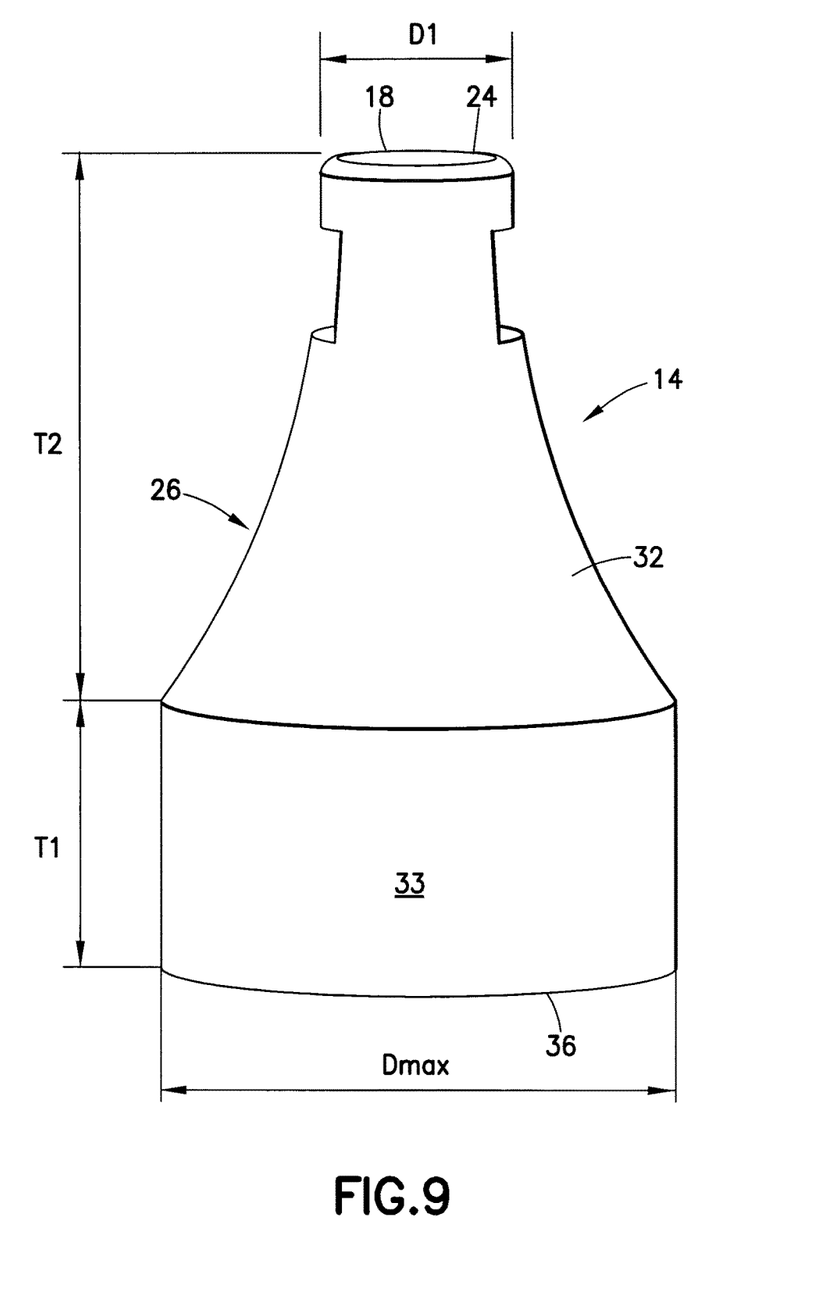
Figure 10:
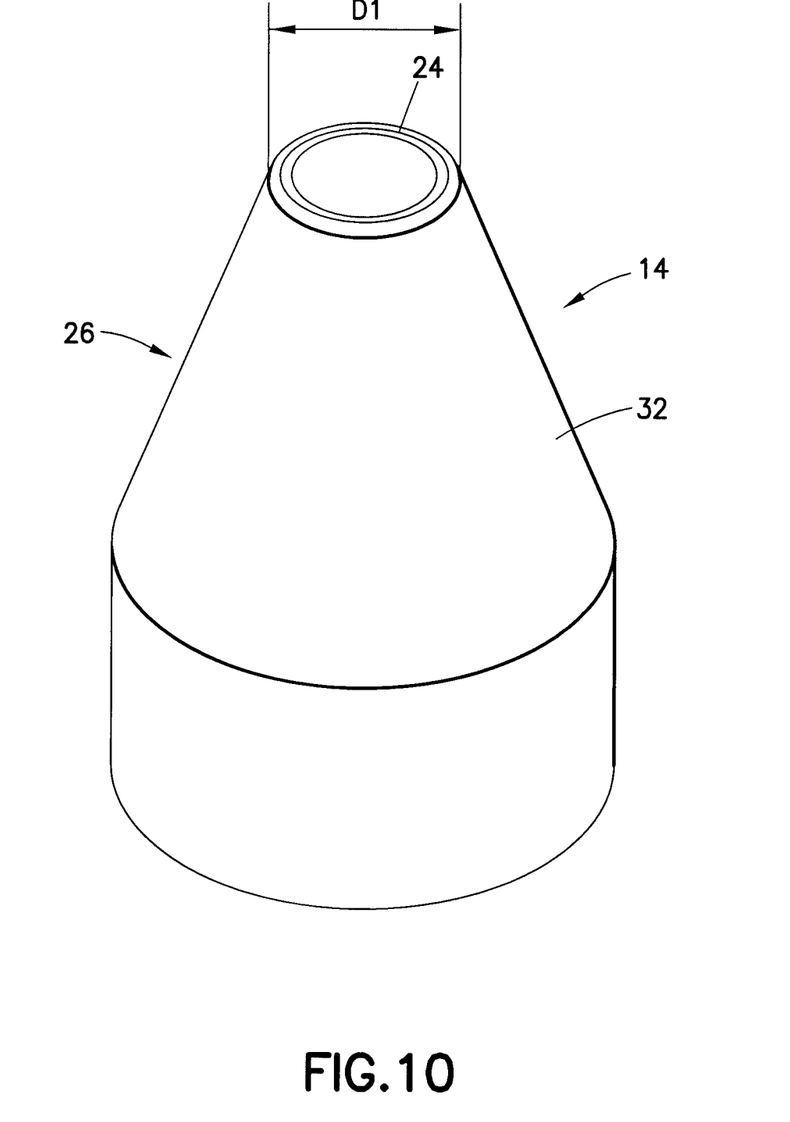
Figure 11:
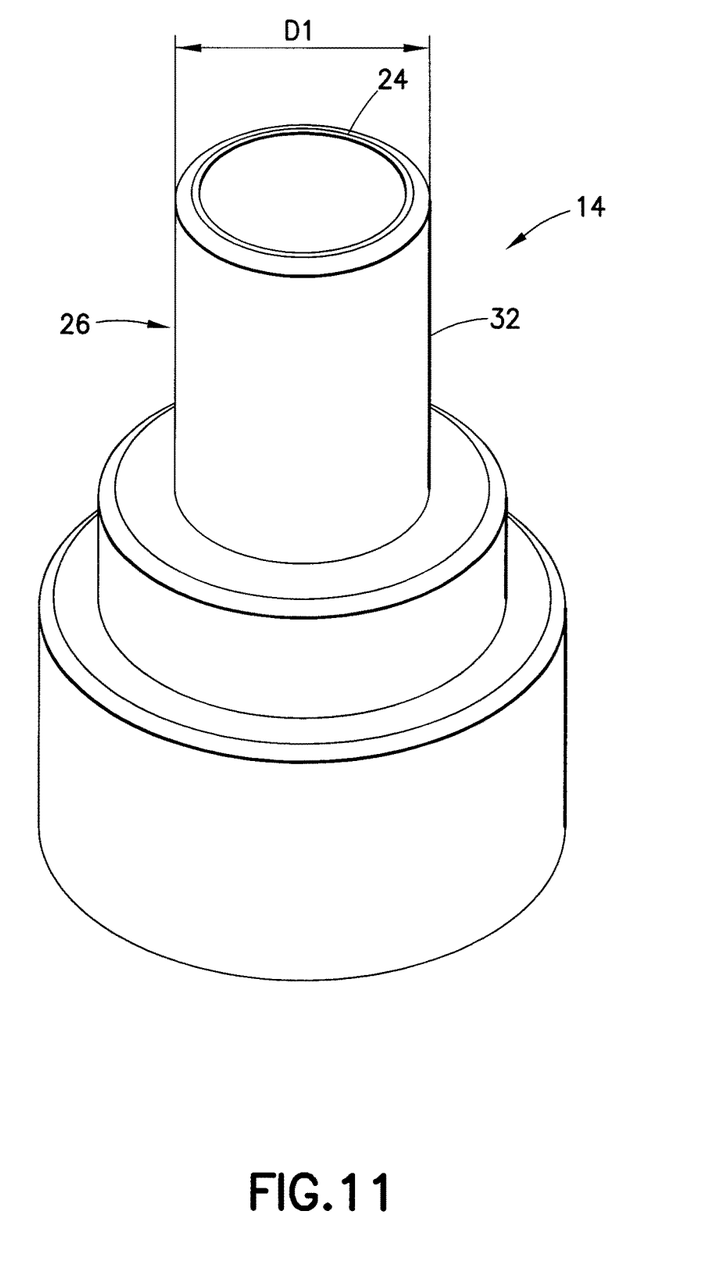

With the subject invention, at least one outer diameter is defined on the outer surface 32 which is greater than the reduced outer diameter D1 at one or more locations located proximally of the reduced outer diameter D1. In this manner, a change in outer diameter is provided on the shield 14 from the distal end 18 proceeding proximally along the shield 14. As shown in FIGS. 8 and 9, the change may be gradual so as to impart a concave configuration to the sidewall 26. Alternatively, the sidewall 26 may have a tapered configuration, as shown in FIG. 10 or a step change, as shown in FIG. 11. Other configurations for the sidewall 26 are possible, which may include arcuate, linear, and/or irregular segments. The concave configuration of the sidewall 26 shown in FIGS. 8 and 9 is preferred.

It is preferred that the outer diameter of the shield 14 be greatest (Dmax) at a location closer to the proximal end 36 of the shield 14 than the distal end 18 of the shield 14. The shield 14 may define a constant section having the greatest outer diameter Dmax, such that a cylinder 33 is defined having the greatest outer diameter Dmax. The cylinder 33 may extend from the proximal end 36 of the shield 14, It is further preferred that the outer diameter of the shield 14 gradually increase from the reduced outer diameter D1 to the greatest outer diameter Dmax.

In a preferred arrangement, the distalmost location of the greatest outer diameter Dmax is located at a distance T1 from the proximal end 36 of the shield 14 and a distance T2 from the distal end 18 of the shield 14, where T2>T1.

With the reduced outer diameter D1 at the distal end 24, the shield 14 may provide the safety needle assembly 10 with a more aesthetically-pleasing appearance, In addition, the distal end may provide a guide for orienting the safety pen needle assembly 10 during an injection.

It is preferred that the distal end 24 be formed with minimal surface area, to limit skin contact area. The distal end 24 may be annular (circumscribing the opening 22) having a width generally equal to the thickness of the sidewall 26. Preferably, the sidewall 26 defines an inner diameter in the range of 0.110-0.325 inches adjacent to the distal end 24 (this inner diameter may be equal to the diameter of the opening 22). To provide added comfort for a patient, a rounded fillet 38 may be provided on the distal end 24 for engagement against a patient's skin. The rounded configuration provides a more comfortable engagement surface during injection.

As will be appreciated by those skilled in the art, the two aspects discussed above may be used in combination or separately.

What is claimed is:

1. A safety needle assembly for an injector comprising:
a needle having a distal end formed for an injection;
a carrier supporting the needle, the carrier being configured for mounting onto the injector; and
a shield covering the distal end of the needle, the shield having at least one window formed therein, wherein the at least one window is superimposed over the distal end of the needle in an initial state prior to the injection as viewed along an axis disposed perpendicularly to the needle, the distal end of the needle being visible through the at least one window in the initial state;
wherein a proximal edge of the at least one window is located proximally of the distal end of the needle in the initial state prior to the injection, the proximal edge being located distally of the distal end of the needle in a post-use state after the injection.

2. The assembly as in claim 1, wherein a distal end of the shield spans across the at least one window.

3. The assembly as in claim 1, wherein the at least one window is provided as at least two windows.

4. The assembly as in claim 1, wherein the shield includes a distal end and a sidewall that extends proximally from the distal end of the shield, the at least one window being formed through the sidewall in proximity to the distal end of the shield; and wherein a distalmost location of a greatest outer diameter of the sidewall is located at a first distance from a proximal end of the shield and at a second distance from the distal end of the shield, where the second distance is larger than the first distance.

5. A safety needle assembly for an injector comprising:
a needle having a distal end formed for an injection;
a carrier supporting the needle, the carrier being configured for mounting onto the injector; and
a shield covering the distal end of the needle, the shield having a proximal end, a distal end, and a sidewall extending therebetween, the sidewall defining a first outer diameter at or adjacent to the distal end of the shield, the sidewall defining a greatest outer diameter, greater than the first outer diameter, at a location closer to the proximal end of the shield than the distal end of the shield, the greatest outer diameter being greater than all outer diameters defined by the sidewall between the location and the first outer diameter;
wherein an outer diameter of the shield gradually increases from the first outer diameter to the greatest outer diameter;
wherein the shield has at least one window, a proximal edge of the at least one window being located proximally of the distal end of the needle in an initial state prior to the injection, the proximal edge being located distally of the distal end of the needle in a post-use state after the injection.

6. The assembly as in claim 5, wherein the shield defines the greatest outer diameter over a length of the shield extending between the location and the proximal end.

7. The assembly as in claim 5, wherein a distalmost location of the greatest outer diameter is located at a first distance from the proximal end of the shield and at a second distance from the distal end of the shield, where the second distance is larger than the first distance; and wherein the sidewall has one of a concave configuration and a tapered configuration proximally of the first outer diameter.

8. A safety needle assembly for an injector comprising:
a needle having a distal end formed for injection;
a carrier supporting the needle, the carrier being configured for mounting onto the injector; and
a shield covering the distal end of the needle, the shield having a proximal end, a distal end, and a sidewall extending therebetween, the sidewall having at least one window;
wherein the at least one window is superimposed over the distal end of the needle in the initial state prior to the injection as viewed along an axis disposed perpendicularly to the needle, and the distal end of the needle is visible through the at least one window; and
wherein in the initial state prior to the injection, a proximal edge of the at least one window is located proximally of the distal end of the needle, the proximal edge being located distally of the distal end of the needle in a post-use state after the injection.

9. The assembly as in claim 8, wherein the sidewall defines:
a first outer diameter at or adjacent to the distal end of the shield;
at least one outer diameter greater than the first outer diameter atone or more locations located proximally of the first outer diameter; and
a greatest outer diameter (Dmax) at a location closer to the proximal end of the shield than the distal end of the shield, wherein a distalmost location of the greatest outer diameter (Dmax) is located at a first distance from the proximal end of the shield and at a second distance from the distal end of the shield, where the second distance is larger than the first distance; and
wherein proximally of the first outer diameter, the sidewall has one of a concave configuration and a tapered configuration.

* * * * *